United States Patent [19]

Hirva et al.

[11] Patent Number: 5,126,304
[45] Date of Patent: Jun. 30, 1992

[54] METHOD FOR THE PREPARATION OF A CATALYST FOR WATER GAS AND HYDROFORMYLATION, CATALYST PREPARED BY THE METHOD AND USE OF THE CATALYST

[75] Inventors: Pipsa Hirva, Kitee; Tapani Pakkanen; Tapani Venäläinen, both of Joensuu; Outi Krause, Sipoo; Leila Alvila, Joensuu, all of Finland

[73] Assignee: Neste Oy, Finland

[21] Appl. No.: 632,185

[22] Filed: Dec. 21, 1990

[30] Foreign Application Priority Data

Jan. 16, 1990 [FI] Finland .................................. 900246

[51] Int. Cl.⁵ ............................................. B01J 31/28
[52] U.S. Cl. .................................... 502/161; 502/167; 423/655; 568/455
[58] Field of Search ........................... 502/161, 167

[56] References Cited

U.S. PATENT DOCUMENTS 4,699,775 10/1987 Verlainen et al. .............. 502/161 X Primary Examiner—Patrick P. Garvin
Attorney, Agent, or Firm—Steinberg & Raskin

[57] ABSTRACT

The invention relates to a method for the preparation of a catalyst for water gas and hydroformylation reactions, which catalyst includes as active components a ruthenic carbonyl and a heterocyclic base on a solid carrier. The catalyst is formed by one or more successive reactions in which the ruthenic carbonyl is fixed from a gas phase onto the carrier and the heterocyclic base is fixed onto the carrier either from a gas phase in the same was as in the case of the ruthenic carbonyl, or from a solution or melt of the heterocyclic base.

13 Claims, 1 Drawing Sheet

METHOD FOR THE PREPARATION OF A CATALYST FOR WATER GAS AND HYDROFORMYLATION, CATALYST PREPARED BY THE METHOD AND USE OF THE CATALYST

BACKGROUND OF THE INVENTION

The transfer reaction $CO+H_2O \rightarrow CO_2+H_2$ of water gas is used for preparing hydrogen e.g. in the ammonia industry, and for increasing the hydrogen content of a synthetic gas, e.g. in the Fischer-Trosch synthesis. The reaction is most advantageous at a low temperature with respect to thermodynamic yield.

The catalysts used in the industry for the transfer reaction of water gas are either mixtures of iron and chrome oxides operating at a high temperature, or mixtures of copper, zinc and aluminum oxides at a lower temperature. Even the last-mentioned catalysts require a temperature of at least 200° C., whereby the conversion of the reaction is partially limited by a reaction balance on the side of the reactants.

One of the most effective catalysts operating at the lowest temperatures of the water-gas transfer reaction is a compound prepared from a ruthenic carbonyl $Ru_3(CO)_{12}$ and a 2,2'-bipyridine and an inorganic oxide (U.S. Pat. No. 4,699,775). The preparation method of the catalyst is based on mixing the reactants in solid or liquid phase, in which case it is difficult to utilize the large specific area of the oxide component in the optimization of the catalyst activity.

Alcohols and aldehydes are generally prepared by means of hydroformylating processes. The catalysts used in industrial processes are generally homogeneous rhodium or cobalt carbonyls or phosphines. However, a heterogenous catalyst is usually easier to use, especially relative to the separation of the products. This advantage is especially emphasized when using expensive rhodium catalysts. The advantages of a heterogenous catalyst also include a higher thermal stability and minor corrosion problems.

A hydroformylating catalyst can also be prepared from ruthenic carbonyl and bipyridine, which catalyst together with an inorganic oxide forms a hetero catalyst system (U.S. patent application Ser. No. 424,289, now U.S. Pat. No. 5,001,685). The catalyst is prepared by admixing a ruthenic carbonyl, a bipyridine and an oxide in an organic solvent, from which the solvent is evaporated. The preparation method cannot effectively utilize the large surface area of the porous oxide component. As a result, the reproducibility of the catalyst preparation is disadvantageous, and the solubility into the product mixture is detrimental to heterogenous catalysis.

SUMMARY OF THE INVENTION

It is a primary object of the present invention to provide an improved method for the preparation of catalysts for water gas and hydroformylation reactions.

It is a further object of the present invention to provide catalysts for water gas and hydroformylation reactions which are prepared by the improved method of the present invention and which therefore have improved properties.

It is yet another object of the present invention to provide for the use of the catalysts produced by the method of the present invention for water gas and hydroformylation reactions, particularly for the preparation of hydrogen gas from carbon monoxide and water, and for the hydroformylation of olefines by carbon monoxide and hydrogen.

Other objects and advantages of the present invention will be apparent from a further reading of the specification and of the appended claims.

The invention according to the application relates to a new catalyst preparation method, wherein the catalyst is synthesized by means of successive controlled reactions. The method is adapted to the preparation of water gas and hydroformylating catalysts formed from a ruthenic carbonyl, a bipyridine and an oxide.

The method according to the invention for preparing a catalyst for water gas and hydroformylating reactions, which catalyst includes as active components a ruthenic carbonyl and heterocyclic base on a solid carrier, is thus characterized in that the catalyst is formed by means of one or more successive reactions, in which the ruthenic carbonyl is fixed from a gas phase onto the carrier and the heterocyclic base is fixed to the carrier either from the gas phase in the same way as the ruthenic carbonyl or from a solution or melt of the heterocyclic base.

In accordance with one of the embodiments of the invention, the catalyst is formed by performing one or more two-reaction cycles, in which the first reaction phase comprises the fixing of the ruthenic carbonyl from a gas phase to the surface of a carrier and the second reaction phase comprises the fixing of a heterocyclic base to the surface of the carrier.

However, a heterocyclic base can as readily be fixed in such way that the carrier treated with the ruthenic carbonyl according to the invention is treated with a heterocyclic-base melt or solution, whereby the base is fixed to the catalyst.

The gas phase including a ruthenic carbonyl and a heterocyclic base advantageously also contains a gas which acts as an inert carrier gas or a gas which acts as a reactive carrier gas. For example, nitrogen, argon or helium can be used as an inert gas and carbon monoxide or hydrogen can be used as a reactive gas.

A catalyst forming according to an embodiment of the invention can at any time before or after each reaction phase, or between the reaction phases be treated with a reactive gas for modifying its properties.

BRIEF DESCRIPTION OF THE DRAWING

The invention is further illustrated in connection with the accompanying drawing in which FIG. 1 diagrammatically illustrates an arrangement for carrying out the method of the present invention.

Figure 1:
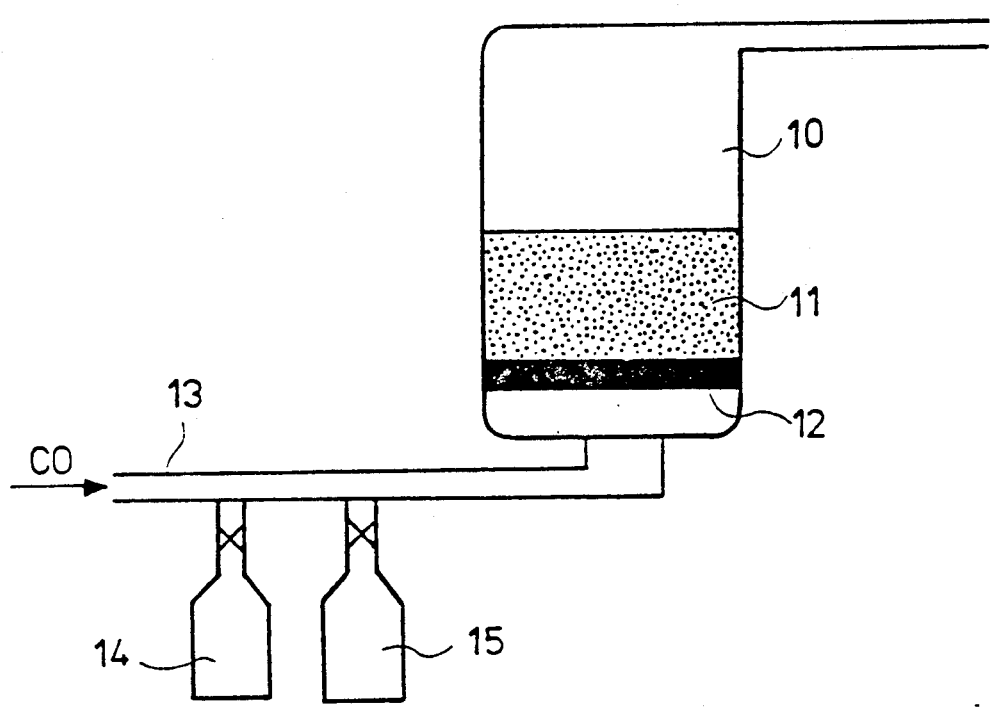
As illustrated in FIG. 1, a reactor 10 is provided with an oxide component 11 which acts as a carrier and is placed at the top of a wire mesh or ceramic sinter 12. A carrier gas is led through line 13 under the wire mesh or ceramic sinter 12. This carrier gas can be either an inert gas, such as nitrogen, argon or helium, or a reactive gas such as carbon monoxide, as desired.

The gas flow forms a fluidized bed, on which the oxide layer 11 is continuously moving. Into the gas flow is led a ruthenic carbonyl $Ru_3(CO)_{12}$, which is sublimated from an oven 14 by a suitable heating means. The ruthenic carbonyl transfers with the carrier gas into the reactor 10, in which it can be adsorbed into the oxide by controlling the temperature. Similarly, a bipyridine can be sublimated from the oven 15.

The quantity of the adsorbing ruthenic carbonyl can be controlled by means of the feeding time of the ruthenic carbonyl and the reactor temperature, whereby a monomolecular overlap, a reduced layer overlap or a multilayer overlap can be selected. The correct temperature and treatment times can be found experimentally, and they are dependent e.g. on the evaporability of the active components used and the pressure conditions. When the ruthenic carbonyl is, for example, $Ru_3(CO)_{12}$, the treatment time can vary very widely e.g. from one second to 30 hours and the temperature can be 50°-200° C. If the preparation of the catalysts is performed by using several successive ruthenic carbonyl-bipyridine pulses, the treatment time in each pulse can be very short. If the ruthenic carbonyl is $Ru(CO)_5$, the temperature used can be even considerably lower, even less than 0° C.

The reactor pressure during the addition of the ruthenic carbonyl can also vary widely e.g. between 10 mbar and 100 bar. However, it is normally possible to operate at close to atmospheric pressure, even though elevated temperatures are also possible.

The ruthenic carbonyl is as such transferred by means of the inert carrier gas to the oxide. If a reactive carrier gas is used, the ruthenic carbonyl can be modified before the adsorption, for example, by decomposing or substituting. The reactive carrier gas can also affect the structure, composition and surface properties of the oxide surface. Gas flows can also be used in the reactor, by means of which the solid components of the catalyst are not transferred, but intermediate reactions are performed, with which the catalyst forming is treated. Such gas flow can, for example, be hydrogen, with which a reduction is performed.

The next phase of the preparation of the ruthenic carbonyl-bipyridine-oxide is the reaction of a 2,2'-bipyridine with a ruthenic carbonyl-oxide complex. This reaction can be performed e.g. in the reactor of the drawing. When the reaction is performed in the reactor, the ruthenic carbonyl oven 14 is kept closed and the bipyridine oven 15 is opened. The oven is heated in such way that the bipyridine is sublimated into the gas flow. In the reactor, the bipyridine immediately reacts with the ruthenic carbonyl - oxide complex. Suitable temperature and treatment times can be determined experimentally, and are generally about 50°-200° C. and between about one second and 20 hours. The reaction can be continued by feeding a new ruthenic carbonyl-bipyridine pulse, whereby the ruthenic-bipyridine-oxide ratio of the catalyst can be adjusted to the optimum value. The catalyst can be further activated in the reactor either by means of heat or gas treatment.

The bipyridine reaction can also be performed in such way that the ruthenic carbonyl-oxide complex is transferred into a molten bipyridine, whereby a catalyst is prepared.

When silica gel $SiO_2$ is used as an oxide and carbon monoxide is used a carrier gas, a new reactive surface complex is formed in the fluidized-bed reactor from the ruthenic carbonyl $Ru_3(CO)_{12}$, the IR spectroscopic properties of which complex clearly deviate from a surface complex prepared with an inert gas or adsorbed from a solution. This new complex immediately reacts with the bipyridine at room temperature.

The $Ru_3(CO)_{12}$-2,2'-bipyridine-silica gel catalyst acts both in the transfer reaction of the water gas and in the hydroformylation of the olefines. The highest activity reached in the water gas reactor 19500 mol $H_2$/mol $Ru_3(CO)_{12}$ * 24 h is 2-4 times greater than the results reported earlier. In hydroformylation, the activities are slightly lower than those reported earlier, but the stability of the catalyst is correspondingly better.

The advantages of the invention described above in comparison with prior art are better controllability of the ruthenic-bipyridine-oxide catalyst and thereby more effective catalysts. The preparation reaction is performed in controlled manner by phases, whereby the quantity of the reactants used correspond only to the quantity with which the oxide surface is ready to react in the different phases of preparation. Each reaction phase can be characterized separately, owing to which a more detailed analysis of the preparation reaction is possible, when comparing the analyzed metal content of the catalyst with a surface area available for oxide adsorption, it can be seen that the change reaction gives with one pulse a clearly lower monomolecular overlap degree. A higher overlap degree can be obtained by changing the reactor temperature or by extending the sublimation time.

In the method according to the invention, the ruthenic carbonyl is preferably $Ru_3(CO)_{12}$. A bipyridine, especially a 2,2'-bipyridine, is preferably used as the heterocyclic base.

Any inorganic oxide can be used as a solid carrier, but an especially preferable oxide is silica. The carrier is preferably dried before the reaction by the ruthenic carbonyl, for example, by heating at about 600° C.

The catalysts prepared by the method according to the invention are especially suitable for the transfer reaction of the water gas for preparing hydrogen gas from carbon monoxide and water, but the same catalysts can also be used in the hydroformylation of olefines into alcohols.

DESCRIPTION OF PREFERRED EMBODIMENTS

The present invention is further illustrated by the following examples. The scope of the invention is not, however, meant to be limited to the specific details of the examples.

EXAMPLE 1

The catalyst was prepared by sublimating $Ru_3(CO)_{12}$ to an oxide on a fluidized bed (silica F-22, dried at 600° C., 2.3 g) in a CO gas flow (flow rate=30 ml/min) for 5 hours at 145° C. The ruthenic content measured with an atomic absorption spectrophotometer (calculated per 1 g of oxide) was 4.7 mg 1.2 g of ruthenic sublimated oxide and 0.2 g of 2,2'-bipyridine were admixed in a $N_2$ atmosphere, evacuated and kept in an oil bath at 80° C. for 3 days.

EXAMPLES 2-5

The process of Example 1 was repeated, except that in Example 2 the sublimation time was 10 hours and the mixture contained 1.7 g of ruthenic-sublimated oxide (determined ruthenic content 11.7 mg/g of oxide); in Example 3 the sublimation time was 15 hours and the quantity of oxide in the mixture was 1.6 g (ruthenic content 16.0 mg/g of oxide); in Example 4 the sublimation time was 20 hours, the flow rate 46 ml/min and the quantity of oxide in the mixture was 1.8 g (ruthenic content 28.0 mg/g of oxide); and in Example 5 the sublimation time was 30 hours and the flow rate 46 ml/min and quantity of oxide 1.8 g (ruthenic content 51.4 mg/g of oxide).

EXAMPLE 6

The catalyst was prepared by sublimating $Ru_3(CO)_{12}$ to an oxide on a fluidized bed (silica F-22, dried at 600° C., 2.5 g) in a CO gas flow for 11.5 hours at 120° C. 2,2'-bipyridine was then sublimated for 11.5 hours at 65° C. The reaction product was kept in an oil bath of 100° C. for 4 days. The determined ruthenic content was 12.1 mg/1 g of the catalyst.

EXAMPLE 7

Example 6 was repeated except that the sublimation time was 1 hour at a time and the cycle was repeated 10 times. After each addition of 2,2'-bipyridine, the catalyst was cured at 100° C. The determined ruthenic content was 5.3 mg/g of the catalyst.

EXAMPLE 8

The catalyst of Example 1 (0.5 g), 1-hexene (1.0 cm$^3$), toluene (5.0 cm$^3$) and benzene (0.2 cm$^3$) were transferred in a nitrogen atmosphere into an autoclave (V=0.09 dm$^3$) and 25 MPa of H$^2$ and 2.5 MPa of CO were added. The autoclave was kept at 150° C. for 17.5 hours. The product mixture was analyzed by means of gas chromatography. The reaction product did not contain alcohols or aldehydes.

EXAMPLE 9

Example 8 was repeated except that the catalyst of Example 2 was used as the catalyst. The reaction product contained 5% of C$_7$ alcohols.

EXAMPLE 10

Example 8 was repeated except that the catalyst of Example 3 was used as the catalyst. The reaction product contained 26% of C$_7$ alcohols.

EXAMPLE 11

Example 8 was repeated except that the catalyst of Example 4 was used as the catalyst. The reaction product contained 35% of C$_7$ alcohols.

EXAMPLE 12

Example 8 was repeated except that the catalyst of Example 5 was used as the catalyst. The reaction product contained 36.5% of C$_7$ alcohols.

EXAMPLE 13

Example 8 was repeated except that the catalyst of Example 6 was used as the catalyst. The reaction product contained 35% of C$_7$ alcohols.

Examples 8-13 show that as the ruthenic content of the catalyst increases, the alcohol conversion increases, but reaches a certain maximum level under the specific hydroformylating conditions.

EXAMPLE 14

Example 13 was repeated except that the reaction time in the hydroformylation was 66 h. The reaction product contained 52% of C$_7$ alcohols.

EXAMPLE 15

The catalyst of Example 7 was tested in a continuous reactor in a water-gas transfer reaction. 1.0 g of the catalyst was packed into a reaction tube (p(CO)=7 bar, P(H$_2$O)=6.5 bar, T=150° C., V=6-40 ml/min), the product gas flowing through was analyzed with a gas chromatograph. The maximum activity obtained was 5800 mol H$_2$/mol Ru$_3$(CO)$_{12}$*24 h.

EXAMPLE 16

Example 15 was repeated except that the catalyst of Example 3 (0.9 g) was used as the catalyst. The maximum activity obtained was 16900 mol H$_2$/mol Ru$_3$(CO)$_{12}$*24 h.

EXAMPLE 17

Example 15 was repeated except that the catalyst of Example 5 (0.7 g) was used as the catalyst. The maximum activity obtained was 19500 mol H$_2$/mol Ru$_3$(CO)$_{12}$*24 h.

While the invention has been illustrated with specific materials and examples, it is apparent that variations and modifications thereof can be made within the scope of the invention.

What is claimed is:

1. Method for the preparation of a water-gas and hydroformylating reaction catalyst, which comprises passing a gaseous ruthenic carbonyl through a fluidized bed or a solid carrier, whereby said ruthenic carbonyl becomes fixed to said carrier, and fixing 2,2'-bipyridine onto said carrier from a gaseous phase, from a solution or by melting of said heterocyclic base.

2. Method according to claim 1 wherein said method is effected in two reaction cycles, each reaction cycle comprising a first phase of fixing of the ruthenic carbonyl from gas phase onto the surface of said carrier and a second phase of fixing of said 2,2'-bipyridine onto the surface of said carrier.

3. Method according to claim 2 wherein said gas phase includes at least one of an inert gas or a reactive gas selected from the group consisting of CO and H$_2$.

4. Method according to claim 3 wherein said inert gas is nitrogen, argon or helium.

5. Method according to claim 3 wherein said reactive gas is contacted with the catalyst before or after each phase, for the purpose of modifying the properties of said catalyst.

6. Method according to claim 4 wherein said reactive gas is contacted with the catalyst before or after each phase, for the purpose of modifying the properties of said catalyst.

7. Method according to claim 1 wherein temperature and treatment times are selected to achieve a monomolecular overlap, reduced layer overlap or multilayer overlap of the active component on the carrier.

8. Method according to claim 2 wherein temperature and treatment times are selected to achieve a monomolecular overlap, reduced layer overlap or multilayer overlap of the active component on the carrier.

9. Method according to claim 1 wherein the ruthenic carbonyl is contacted with the carrier in a gas phase which contains carbon monoxide.

10. Method according to claim 2 wherein the ruthenic carbonyl is contacted with the carrier in a gas phase which contains carbon monoxide.

11. Method according to claim 1 wherein the ruthenic carbonyl is Ru$_3$(CO)$_{12}$ or Ru(CO)$_5$.

12. Method according to claim 1 wherein the solid carrier is an inorganic oxide.

13. Method according to claim 1 wherein the solid carrier is silica.

* * * * *